(12) United States Patent
Moriarty et al.

(10) Patent No.: US 9,403,837 B2
(45) Date of Patent: Aug. 2, 2016

(54) STEREOSELECTIVE TOTAL SYNTHESIS OF NORIBOGAINE

(71) Applicant: DemeRx, Inc., Fort Lauderdale, FL (US)

(72) Inventors: Robert M. Moriarty, Michiana Shores, IN (US); Deborah C. Mash, Fort Lauderdale, FL (US)

(73) Assignee: DEMERX, INC., Fort Lauderdale, FL (US)

( * ) Notice: Subject to any disclaimer, the term of this patent is extended or adjusted under 35 U.S.C. 154(b) by 94 days.

(21) Appl. No.: 14/486,804

(22) Filed: Sep. 15, 2014

(65) Prior Publication Data

US 2015/0005492 A1    Jan. 1, 2015

Related U.S. Application Data

(62) Division of application No. 13/708,834, filed on Dec. 7, 2012, now Pat. No. 8,937,061.

(60) Provisional application No. 61/568,568, filed on Dec. 8, 2011.

(51) Int. Cl.
*C07D 453/06* (2006.01)
*C07D 487/22* (2006.01)
*C07D 471/18* (2006.01)

(52) U.S. Cl.
CPC ............ *C07D 487/22* (2013.01); *C07D 471/18* (2013.01)

(58) Field of Classification Search
CPC ...................................................... C07D 453/06
USPC ........................................................ 540/579
See application file for complete search history.

(56) References Cited

U.S. PATENT DOCUMENTS

| 2,813,873 | A | 11/1957 | Janot et al. |
| 3,716,528 | A | 2/1973 | Nagata et al. |
| 5,616,575 | A | 4/1997 | Efange et al. |
| 6,348,456 | B1 | 2/2002 | Mash et al. |
| 7,220,737 | B1 | 5/2007 | Mash |
| 2013/0165647 | A1 | 6/2013 | Moriarty et al. |

OTHER PUBLICATIONS

Corey, E.J., "Catalytic Enantioselective Diels-Alder Reactions: Methods, Mechanistic Fundamentals, Pathways, and Applications," Angew. Chem. Int. Ed., (2002), 41:1650-1667.
Futatsugi, et al., "Oxazaborolidine-Derived Lewis Acid Assited Lewis Acid as a Moisture-Tolerant Catalyst for Enantioselective Diels-Alder Reactions," Angew. Chem. Int. Ed., (2005), 44:1484-1487.
International Search Report and Written Opinion dated Mar. 13, 2013 in related PCT Patent Application No. PCT/US2012/067629.
Kagan, et al., "Catalytic Asymmetric Diels-Alder Reactions," Chem. Rev., (1992), 92:1007-1019.
Trost, et al., "A Total Synthesis of Racemic and Optically Active Ibogamine. Utilization and Mechanism of a New Silver Ion Assisted Palladium Catalyzed Cyclization," J. Am. Chem. Soc., (1978), 100(12):3930-3931.
Trost, et al., "Stereocontrolled Approach to 1,4-Disubstitued 1,3-Dienes," J. Org. Chem., (1978), 43(24):4559-4564.
Notification of Defects in Application issued on Israeli Application 232724, mailed Nov. 4, 2015.
Office Action on Chinese Application 201280058362.5, issued Aug. 5, 2015, English translation provided.

*Primary Examiner* — Brenda Coleman
(74) *Attorney, Agent, or Firm* — Foley & Lardner LLP

(57) ABSTRACT

This invention relates generally to methods for synthesizing the non-addictive alkaloid noribogaine.

9 Claims, No Drawings

STEREOSELECTIVE TOTAL SYNTHESIS OF NORIBOGAINE

CROSS-REFERENCE TO RELATED APPLICATION

This application is a divisional of U.S. patent application Ser. No. 13/708,834, filed on Dec. 7, 2012, entitled "STEREOSELECTIVE TOTAL SYNTHESIS OF NORIBOGAINE," which claims the benefit under 35 U.S.C. §119 (e) of U.S. Provisional Application No. 61/568,568, filed Dec. 8, 2011, entitled "STEREOSELECTIVE TOTAL SYNTHESIS OF NORIBOGAINE," which are incorporated herein by reference in their entirety.

FIELD OF THE INVENTION

This invention relates generally to methods for synthesizing the non-addictive alkaloid noribogaine. This invention is further directed to intermediates used in the chiral directed synthesis of noribogaine.

STATE OF THE ART

Noribogaine is a well known member of the ibogaine family of alkaloids and is sometimes referred to as 12-hydroxyibogaine. U.S. Pat. No. 2,813,873 claims noribogaine albeit as "12-O-demethylibogaine" while providing an incorrect structural formula for ibogaine. The structure of noribogaine has now been determined and found to combine the features of tryptamine, tetrahydrohavaine and indolazepines. Noribogaine can be depicted by the following formula:

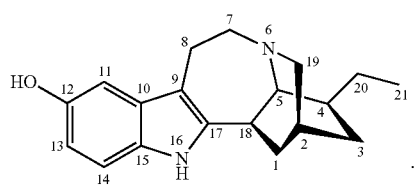

where the configuration at the 2, 4, 5, 6 and 18 atoms are 2(R), 4(S), 5(S), 6(S) and 18(R).

Noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737).

Conventionally, noribogaine is prepared by the O-demethylation of naturally occurring ibogaine:

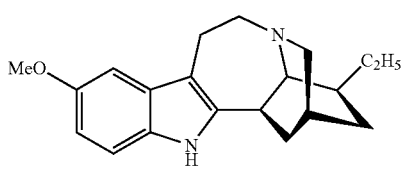

which is isolated from *Tabernanth iboga*, a shrub of West Africa. Demethylation may be accomplished by conventional techniques such as by reaction with boron tribromide/methylene chloride at room temperature followed by conventional purification.

Ibogaine possesses hallucinogenic properties and is a Schedule 1-controlled substance as provided by the US Food and Drug Administration. Accordingly, methods for preparing noribogaine from ibogaine require high levels of assurance that contamination with unacceptable levels of ibogaine is avoided. As above, a one-step method for preparation of noribogaine from ibogaine via O-demethylation does not provide the requisite assurance that ibogaine will consistently be removed as a potential contaminant.

Accordingly, there is an ongoing need to provide a method for preparing noribogaine free from any ibogaine contamination. In addition, there is a limited quantity of ibogaine available since commercially available ibogaine is isolated as a natural product. The total synthesis of noribogaine would avoid such resource depletion.

SUMMARY OF THE INVENTION

This invention provides methods and compositions for the total synthesis of noribogaine. In particular, this invention employs the use of chiral reagents to effect more efficient separation of noribogaine or intermediates during the preparation of noribogaine by providing at least one stereochemical center which could be used to facilitate stereochemical separation. Further, such methods provide noribogaine wherein the ibogaine contamination is eliminated (e.g., less than about 100 ppm).

Accordingly, in one of its composition aspects, this invention is directed to a compound of formula 1a:

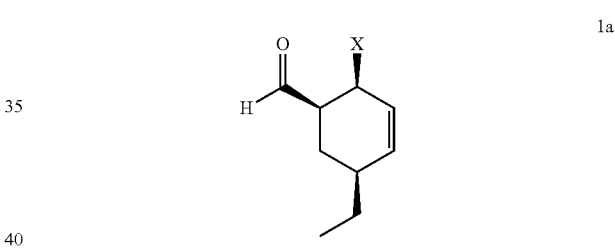

where X is a palladium reactive functional group or precursor thereof. In some embodiments, X is acyloxy, hydroxyl, phosphate, phosphate ester, —OS(O)$_2$OH, —OS(O)$_2$OR$^9$ where R$^9$ is optionally substituted alkyl, cycloalkyl, aryl, heterocycloalkyl or heteroaryl, or —OR$^8$ where R$^8$ is a hydroxyl protecting group. In some embodiments, X is acyloxy having the formula —OC(O)R$^1$, where R$^1$ is an optionally substituted alkyl, cycloalkyl, aryl, heterocycloalkyl or heteroaryl group or a chiral directing group. In certain embodiments, compound 1a is at least 95% the 1S,4S,6R configuration.

In one of its method aspects, this invention is directed to a method for preparing noribogaine 1

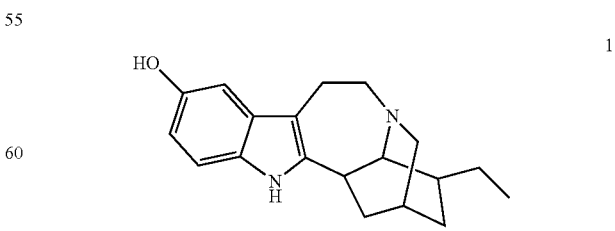

which method comprises the steps of:
a) contacting a compound of formula 1a with a compound of formula 1b, wherein X is a palladium reactive functional group or precursor thereof and $R^2$ and $R^3$ are hydrogen or a protecting group and wherein 1a is at least 95% the 1S,4S,6R configuration,

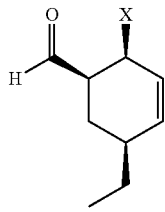

1a

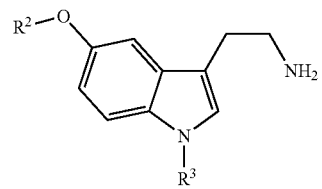

1b under reductive amination reaction conditions to yield a compound of formula 1c:

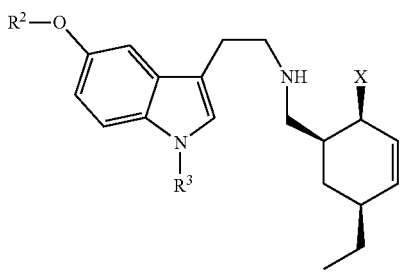

1c b) contacting a compound of formula 1c with a cyclization catalyst under cyclizing conditions to yield a compound of formula 1d:

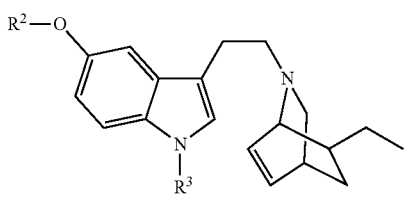

1d c) contacting a compound of formula 1d under olefin arylation conditions to yield a compound of formula 1e:

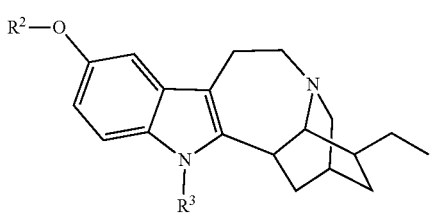

1e d) contacting a compound of formula 1e under deprotection conditions to yield a compound of formula 1;

e) optionally converting compound of formula 1 to its pharmaceutically acceptable salt.

In another of its method aspects, this invention provides for the use of a chiral substituted indole compound in the reaction scheme above to yield a chiral center in compound 1c, 1d or 1e so as to facilitate separation of enantiomers. In one embodiment, compound 1b is replaced with a compound of formula 2b in the process described above:

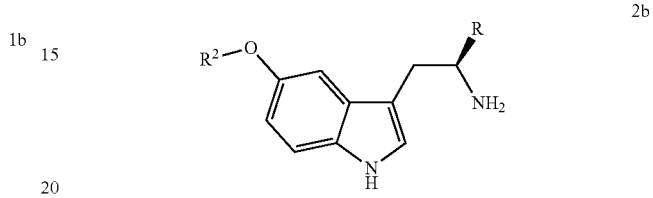

2b where R is selected from the group consisting of carboxyl (derived from 5-hydroxytryptophan), carboxyl ester, amide, phosphonate, phosphonate ester, a peptide, a peptidomimetic, a biodegradable, biocompatible polymer, and —C(O)R$^8$ where R$^8$ is —NH(CH$_2$)$_n$S(O)$_2$OH, —NH(CH$_2$)$_n$OH, —C(O)R$^9$, —OC(O)R$^9$, —CH$_2$C(O)R$^9$, or —CH$_2$C(O)OR$^9$ where R$^9$ is optionally substituted alkyl, cycloalkyl, aryl, heterocycloalkyl or heteroaryl and n is 2-5. Although the S-enantiomer of 2b is depicted, it is contemplated that either the R- or S-enantiomer will preferentially facilitate the separation of enantiomers.

In such methods, noribogaine 1

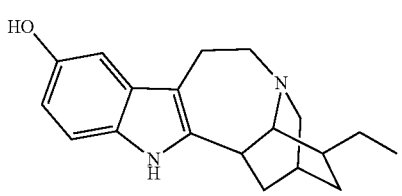

1 is prepared by employing compound 2b in the process described above so as to yield a compound 2c, 2d or 2e (which for illustrative purposes is shown below for compound 2e):

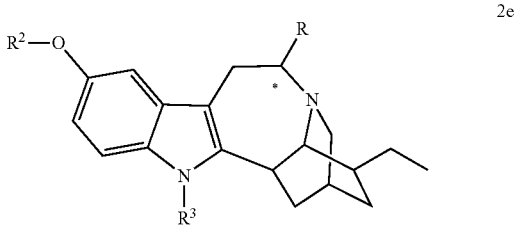

2e

The stereogenic carbon at the 7-position (denoted with an *) of the protected noribogaine structure serves to provide for chiral facilitated separation of stereoisomers at this point of the synthesis. Subsequent removal of the R group can be achieved by conventional conversion of the R group to the corresponding carboxylic acid and decarboxylating to yield compound 1e.

In another of its method aspects, this invention a for preparing formula 2e

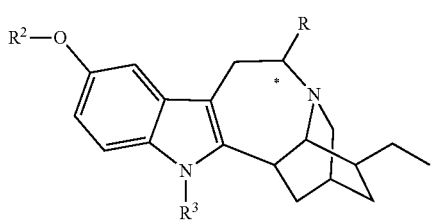

which method comprises:

a) contacting a compound of formula 1a with a compound of formula 2b, wherein R is selected from the group consisting of carboxyl, carboxyl ester, amide, phosphonate, phosphonate ester, a peptide, a peptidomimetic, a biodegradable, biocompatible polymer, and —C(O)R$^8$ where R$^8$ is —NH(CH$_2$)$_n$S(O)$_2$OH, —NH(CH$_2$)$_n$OH, —C(O)R$^9$, —OC(O)R$^9$, —CH$_2$C(O)R$^9$, or —CH$_2$C(O)OR$^9$ where R$^9$ is optionally substituted alkyl, cycloalkyl, aryl, heterocycloalkyl or heteroaryl and n is 2-5, X is a palladium reactive functional group or precursor thereof, R$^2$ is hydrogen or a protecting group, and R$^3$ is hydrogen or a protecting group, and wherein the * denotes a stereogenic carbon having greater than 95% of one enantiomer,

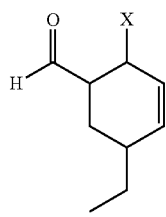

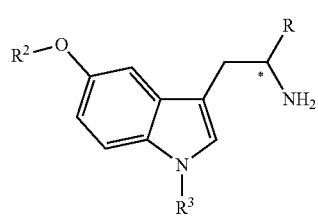

under reductive amination conditions to yield a compound of formula 2c:

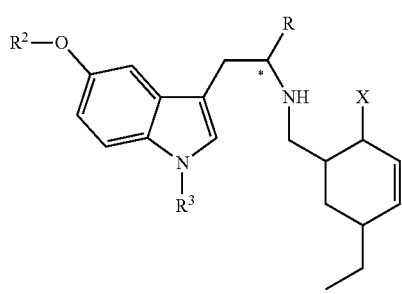

b) contacting a compound of formula 2c with a cyclization catalyst under cyclizing conditions to yield a compound of formula 2d: and

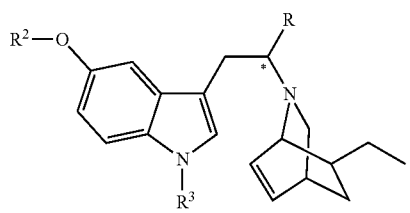

c) contacting a compound of formula 2d under olefin arylation conditions to yield a compound of formula 2e.

The methods disclosed herein provide for the synthesis of noribogaine wherein greater than 90% percent is of the 2R, 4S, 5S, 18R stereochemical configuration. In some embodiments, the methods disclosed herein further comprise the step of further separating two or more stereoisomers.

The compounds as disclosed herein can be used in compositions for treating pain and/or addiction in a patient in need thereof.

DETAILED DESCRIPTION OF THE INVENTION

This invention is directed to methods for the total synthesis of noribogaine and, in particular, methods and compositions comprising stereochemically pure noribogaine and derivatives thereof. However, prior to describing this invention in greater detail, the following terms will first be defined.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a purification step" includes a plurality of such steps.

1. Definitions

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

As stated above, the invention is directed to the total synthesis of noribogaine.

As used herein, the term "noribogaine" refers to the compound:

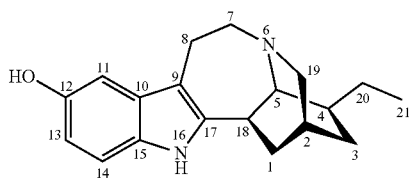

as well as its pharmaceutically acceptable salts thereof. Conventionally, noribogaine is prepared by O-demethylation of naturally occurring ibogaine:

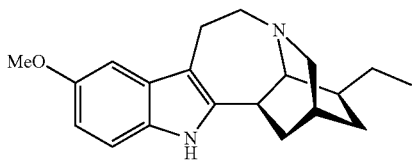

which is isolated from *Tabernanth iboga*, a shrub of West Africa. Demethylation may be accomplished by conventional techniques such as by reaction with boron tribromide/methylene chloride at room temperature followed by conventional purification.

Carbon atoms marked with an asterisk (*) are stereogenic carbon atoms where the absolute configuration of the atom is either greater than about 95% R or greater than about 95% S.

As used herein, the term "reaction conditions" refers to details under which a chemical reaction proceeds. Examples of reaction conditions include, but are not limited to, one or more of following: reaction temperature, solvent, pH, pressure, reaction time, mole ratio of reactants, the presence of a base or acid, or catalyst, etc. Reaction conditions may be named after the particular chemical reaction in which the conditions are employed, such as, decarboxylation conditions, olefin arylation conditions, anhydrous reaction conditions, etc. Reaction conditions for known reactions are generally known to those skilled in the art.

As used herein, the term "anhydrous reaction conditions" refers to reaction conditions wherein water is excluded. Such conditions are known to one of skill in the art, and typically comprise one or more of dry or distilled solvents and reagents, dried reaction vessels, the presence of a drying agent, such as activated molecular sieves, magnesium sulfate, sodium sulfate, etc.

As used herein, the term "reducing agent" refers to a reagent which can donate electrons in an oxidation-reduction reaction, allowing hydrogen to be added to a molecule. Suitable reducing agents include lithium aluminum hydride, sodium borohydride, sodium cyanoborohydride, and the like.

As used herein, the term "reductive amination conditions" refers to the reaction between an amine and a carbonyl compound to form an imine, which is subsequently reduced to an amine using a reducing agent. The intermediate imine can either be isolated and purified prior to the reducing step, or used in the reducing step without prior isolation or purification.

As used herein, the term "cyclization catalyst" refers to a catalyst which facilitates the cyclization between an appropriately functionalized cyclohexene (e.g. cyclohex-2-enyl ester) and an amine. Such catalysts include palladium catalysts such as $Pd(PPh_3)_4$.

As used herein, the term "olefin arylation conditions" refers to reaction conditions under which a covalent bond is formed between a olefin and an aryl or heteroaryl group. The reaction results in the overall reduction of the olefin and retention of the aromaticity of the aryl or heteroaryl group. Such reaction conditions include one or more catalysts such as $(CH_3CN)_2PdCl_2$ and $AgBF_4$.

As used herein, the term "decarboxylation conditions" refers to reaction conditions in which a carboxylic acid or an ester is replaced by a hydrogen. Typically, decarboxylation reactions result in the release of carbon dioxide. In certain embodiments, the decarboxylation conditions first comprise hydrolysis of an ester to the corresponding carboxylic acid using e.g. sodium hydroxide. The decarboxylation can be accomplishing using standard decarboxylation reactions, such as the use of lead tetraacetate followed by hydride reduction of the resultant imine or under standard Barton reaction conditions. The decarboxylation reaction conditions can comprise heat and/or radical initiation. The art is replete with such procedures.

"Alkyl" refers to groups having from 1 to 6 carbon atoms and more preferably 1 to 3 carbon atoms. The alkyl group may contain linear or branched carbon chains. This term is exemplified by groups such as methyl, ethyl, n-propyl, iso-propyl, n-butyl, t-butyl, n-pentyl and the like. The term "$C_x$ alkyl" refers to an alkyl group having x carbon atoms, wherein x is an integer, for example, $C_3$ refers to an alkyl group having 3 carbon atoms.

"Aryl" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Heteroaryl" refers to an aromatic group of from 1 to 10 carbon atoms and 1 to 4 heteroatoms selected from the group consisting of oxygen, nitrogen, sulfur within the ring, wherein the nitrogen and/or sulfur atom(s) of the heteroaryl are optionally oxidized (e.g., N-oxide, —S(O)— or —S(O)$_2$—). Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Examples of heteroaryls include pyridyl, pyrrolyl, indolyl, thiophenyl, and furyl.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic heterocyclic ring. In one embodiment, the nitrogen and/or sulfur atom(s) of the heterocyclic group are optionally oxidized to provide for the N-oxide, sulfinyl, and/or sulfonyl moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

As used herein, the term "optionally substituted alkyl, cycloalkyl, aryl, heterocycloalkyl or heteroaryl group" refers to an alkyl, cycloalkyl, aryl, heterocycloalkyl or heteroaryl group as defined herein optionally substituted with 1 to 3 substituents selected from the group consisting of alkyl, cycloalkyl, aryl, heterocycloalkyl, heteroaryl, halo, —OR$^{10}$, —SR$^{10}$, —CN, —NO$_2$, —C(O)R$^{10}$, —C(O)OR$^{10}$, —NR$^{10}$R$^{10}$, —S(O)R$^{10}$, —S(O)$_2$R$^{10}$, —S(O)$_2$, OR$^{10}$, —OS(O)$_2$R$^{10}$, —OS(O)$_2$OR$^{10}$, —S(O)NR$^{10}$R$^{10}$, —S(O)$_2$NR$^{10}$R$^{10}$, —C(O)NR$^{10}$R$^{10}$, —NR$^{10}$C(O)NR$^{10}$R$^{10}$, and —NR$^{10}$C(S)NR$^{10}$R$^{10}$; and wherein R$^{10}$ is independently hydrogen, alkyl, cycloalkyl, aryl, heterocycloalkyl or heteroaryl.

"Halo" or "halogen" refers to fluoro, chloro, bromo and iodo and preferably is fluoro or chloro.

"Carboxyl" refers to the group "—C(O)OH".

"Carboxyl ester" refers to the group "—C(O)OR$^9$" where R$^9$ is an optionally substituted alkyl, cycloalkyl, aryl, heterocycloalkyl or heteroaryl group.

"acyloxy" refers to the group "—OC(O)R$^9$" where R$^9$ is an optionally substituted alkyl, cycloalkyl, aryl, heterocycloalkyl or heteroaryl group.

"Phosphate" refers to the groups —OP(O)(OH)$_2$ (monophosphate), —OP(O)(OH)OP(O)(OH)$_2$ (diphosphate) and —OP(O)(OH)OP(O)(OH)OP(O)(OH)$_2$ (triphosphate) or salts thereof including partial salts thereof including partial salts thereof. The term "phosphate ester" includes esters of the mono-, di- and tri-phosphate groups described above wherein one or more of the hydrogens are replaced by an R$^9$, where R$^9$ is an optionally substituted alkyl, cycloalkyl, aryl, heterocycloalkyl or heteroaryl group.

"Phosphonate" refers to the groups —P(O)(OH)$_2$ (monophosphonate), —P(O)(OH)OP(O)(OH)$_2$ (diphosphonate) and —P(O)(OH)OP(O)(OH)OP(O)(OH)$_2$ (triphosphonate) or salts thereof including partial salts thereof including partial salts thereof. The term "phosphonate ester" includes esters of the mono-, di- and tri-phosphonate groups described above wherein one or more of the hydrogens are replaced by an R$^9$, where R$^9$ is an optionally substituted alkyl, cycloalkyl, aryl, heterocycloalkyl or heteroaryl group.

"Amide" refers to the groups —C(O)NH$_2$, —C(O)NHR$^9$ and —C(O)N(R$^9$)$_2$ where R$^9$ is an optionally substituted alkyl, cycloalkyl, aryl, heterocycloalkyl or heteroaryl group.

As used herein, the term "peptide" refers to a chain of from 1 to 5 α-amino acids linked by amide bonds (i.e. —NH—C(O)—). The amino acids can be naturally occurring or synthetic amino acids.

As used herein, the term "peptidomimetic" refers to a peptide-like chain designed to mimic a peptide. Peptidomimetics as used herein can include one or more amino acid mimetics, such as, but are not limited to, β2- and β3-amino acids, β-2,2-β-2,3, and (β3-3,3-disubstituted amino acids, α,α-disubstituted amino acids, D-amino acids, optionally substituted α-hydroxyacids, optionally substituted β-hydroxyacids, α-aminonitriles, N-alkylamino acids, and the like. In addition, the C-terminus of the peptidomimetic might be carboxylic acid or carboxamide, or other functional group resulting from the incorporation of one of the above mentioned amino acid mimetics.

As used herein, the term "biodegradable, biocompatible polymer" refers to a polymer which degrades in the body and does not itself or the degradation products thereof produce unacceptable toxicity or injurious side-effects on the biological systems of the mammal. A variety of natural and synthetic polymers have been explored for the preparation of nanoparticles, of which poly(lactic acid) (PLA), poly(glycolic acid) (PGA), and their copolymers (PLGA) have been extensively investigated because of their biocompatibility and biodegradability. Suitable biodegradable polymers for preparing a nanoparticle of the invention include, but are not limited to, poly(lactide-co-glycolides), poly(lactic acid), poly(alkylene glycol), poly(butyl)cyanoacrylate, poly(methylmethacrylate-co-methacrylic acid), poly-allylamine, polyanhydride, polyhydroxybutyric acid, or polyorthoesters and the like.

As used herein, the term "chiral directing group" refers to an optically active chemical moiety that is incorporated into the compound so that a chemical transformation can be carried out stereoselectively to yield the desired product having at least 95% of the desired configuration. Typically, chiral directing groups are removed and are not a part of the desired final product. The chiral directing group can have more than one chiral center. Suitable chiral directing groups can be derived from, in particular, alcohols, α or β-amino acids, carboxylic acids, and the like. Exemplary groups are shown below, where R$^{20}$ and R$^{21}$ are selected from groups such as optionally substituted alkyl (e.g., methyl, iso-propyl, tert-butyl), aryl (e.g., phenyl, biphenyl, 2,6-dimethylphenyl), heteroaryl (e.g., pyridinyl, oxazolyl, etc.), R$^{22}$ and R$^{23}$ are selected from hydrogen and groups such as optionally substituted alkyl (e.g., methyl, iso-propyl, tert-butyl), aryl (e.g., phenyl, biphenyl, 2,6-dimethylphenyl), heteroaryl (e.g., pyridinyl, oxazolyl, etc.), or two of R$^{20}$ and R$^{21}$ or R$^{20}$ and R$^{23}$ together with the atom to which they are attached form an optionally substituted cycloalkyl or heterocycloalkyl ring, and further wherein R$^{20}$, R$^{21}$ and R$^{22}$ are different.

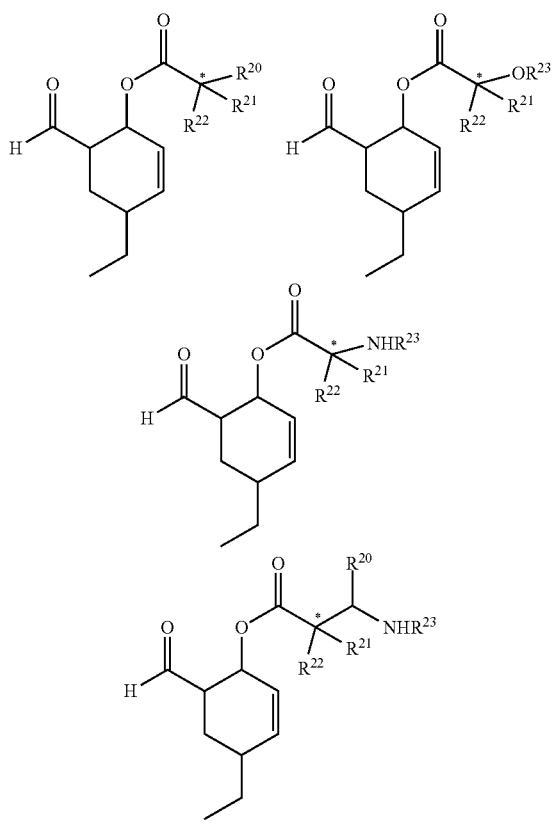

As used herein, the term "palladium reactive functional group" refers to functional groups which can either directly react with palladium, or a precursor to such a group, such that the functional group reacts with a cyclization catalyst under cyclization conditions. Suitable groups include, but are not limited to, acyloxy, hydroxyl, phosphate, phosphate ester, —OS(O)$_2$OH, —OS(O)$_2$OR$^9$ where R$^9$ is optionally substituted alkyl, cycloalkyl, aryl, heterocycloalkyl or heteroaryl, or —OR$^8$ where R$^8$ is a hydroxyl protecting group.

As used herein, the term "pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

As used herein, the term "protecting group" or "Pg" refers to well known functional groups which, when bound to a functional group, render the resulting protected functional group inert to the reaction conditions to be conducted on other portions of the compound and which, at the appropriate time, can be reacted to regenerate the original functionality under "deprotection conditions". The identity of the protecting group is not critical and is selected to be compatible with the remainder of the molecule. In one embodiment, the protecting group is an "amino protecting group" which protects the amino functionality of ibogaine or noribogaine during the reactions described herein. Examples of conventional amino protecting groups include, for instance, benzyl, acetyl, oxyacetyl, carboxybenzyl (Cbz), and the like. In another embodiment, the protecting group is a "hydroxy protecting group" which protects the hydroxyl functionality of noribogaine. Examples of hydroxyl protecting groups include, for instance, benzyl, p-methoxybenzyl, p-nitrobenzyl, allyl, trityl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, Protective Groups in Organic Synthesis., 2d Ed., 1991, John Wiley & Sons, and McOmie Protective Groups in Organic Chemistry, 1975, Plenum Press. Methods for protecting and deprotecting the phenolic hydroxyl group of the compounds disclosed herein can be found in the art, and specifically in Greene and Wuts, supra, and the references cited therein.

As used herein, the term "therapeutically effective amount" refers to the amount of a composition of this invention that is sufficient to effect treatment, as defined herein, when administered to a subject in need of such treatment. The therapeutically effective amount will vary depending upon the subject and condition being treated, the weight and age of the subject, the severity of the condition, the particular composition or excipient chosen, the dosing regimen to be followed, timing of administration, the manner of administration and the like, all of which can be determined readily by one of ordinary skill in the art.

As used herein, the term "treatment" or "treating" means any treatment of a disease or condition in a patient, including:
preventing or protecting against the disease or condition, that is, causing the clinical symptoms not to develop, for example, in a subject at risk of suffering from such a disease or condition, thereby substantially averting onset of the disease or condition;
inhibiting the disease or condition, that is, arresting or suppressing the development of clinical symptoms; and/or
relieving the disease or condition that is, causing the regression of clinical symptoms.

As used herein, the term "pain" refers to all types of pain, including neuropathic and nociceptive pain. It is also contemplated that the compositions disclosed herein can be used to treat other types of pain such as phantom pain which is the sensation of pain from a limb or organ that has been lost or from which a person no longer receives physical signals, and is an experience almost universally reported by amputees and quadriplegics.

As used herein, the term "addiction" refers to a persistent behavioral pattern marked by physical and/or psychological dependency to a substance, particularly drugs such as narcotics, stimulants, and sedatives, including but not limited to heroin, cocaine, alcohol, nicotine, caffeine, amphetamine, desoxyephedrine, methadone and combinations thereof. As used herein, the "treatment of addiction in a patient" refers to reducing the withdrawal symptoms associated with drug dependency as well as alleviating drug cravings in addicts. Such symptoms include nausea, vomiting, anxiety, abdominal cramps, muscle pain, chills and headache.

As used herein, the term "patient" refers to mammals and includes humans and non-human mammals.

Total Synthesis of Noribogaine

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Fourth Edition, Wiley, N.Y., 2007, and references cited therein.

Furthermore, the methods of this invention will typically result in compounds and intermediates with one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Accordingly, in one of its method aspects, this invention is directed to a method for preparing noribogaine 1

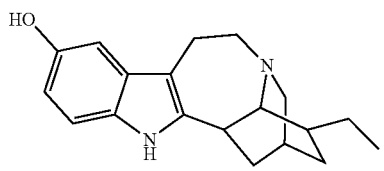

which method comprises the steps of:

a) contacting a compound of formula 1a with a compound of formula 1b, wherein X is a palladium reactive functional group or precursor thereof and $R^2$ and $R^3$ are hydrogen or a protecting group and wherein 1a is at least 95% the 1S,4S,6R configuration,

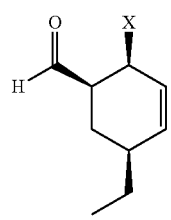

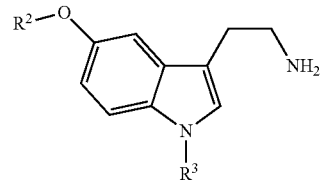

under reductive amination reaction conditions to yield a compound of formula 1c:

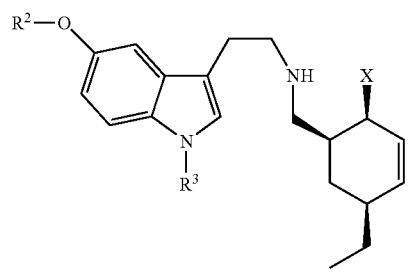

b) contacting a compound of formula 1c with a cyclization catalyst under cyclizing conditions to yield a compound of formula 1d:

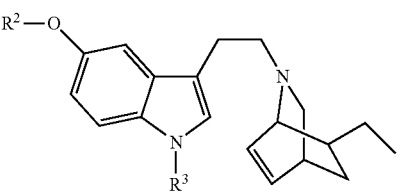

c) contacting a compound of formula 1d under olefin arylation conditions to yield a compound of formula 1e:

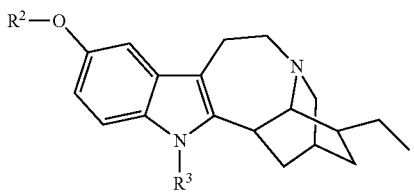

d) optionally contacting a compound of formula 1e under deprotection conditions to yield a compound of formula 1; and e) optionally converting compound of formula 1 to its pharmaceutically acceptable salt.

In the methods disclosed above, the indole nitrogen can further be protected with an amino protecting group ($R^3$) and deprotected as required using amine protecting groups as defined herein. The amino protecting group $R^3$ can be the same as the hydroxyl protecting group $R^2$ (e.g., optionally substituted benzyl) or can be an orthogonal protecting group.

In some embodiments, the reductive amination conditions comprise anhydrous reaction conditions. In some embodiments, the reductive amination conditions of step a) comprise magnesium sulfate. In some embodiments, step a) further comprises low temperatures (e.g. −10 to −5° C.).

In some embodiments, the reductive amination conditions of step a) comprises sodium borohydride ($NaBH_4$). In some embodiments, the reductive amination conditions of step a) comprises sodium cyanoborohydride ($NaBH_3(CN)$). In some embodiments, step a) further comprises raising the temperature when the reducing agent is added (e.g. 0° C.).

In some embodiments, the cyclization catalyst of step b) comprises $Pd(PPh_3)_4$. In some embodiments, $Pd(PPh_3)_4$ is added in an amount ranging from about 3% to about 6%. In some embodiments, step b) further comprises elevated temperatures (e.g. 70° C.).

In some embodiments, the olefin arylation conditions of step c) comprises $(CH_3CN)_2PdCl_2$ and $AgBF_4$. In some embodiments, step c) further comprises a base such as triethylamine. In some embodiments, step c) further comprises adding a reducing agent such as sodium borohydride ($NaBH_4$). In some embodiments, step c) further comprises elevated temperatures (e.g. 70° C.).

In another of its method aspects, this invention is directed to a method for preparing noribogaine 1 from a compound of formula 2e as shown in Scheme 1. In Scheme 1, R is selected from the group consisting of carboxyl, carboxyl ester, amide, phosphonate, phosphonate ester, a peptide, a peptidomimetic, a biodegradable, biocompatible polymer, and —C(O)$R^8$ where $R^8$ is —NH(CH$_2$)$_n$S(O)$_2$OH, —NH(CH$_2$)$_n$OH, —C(O)$R^9$, —OC(O)$R^9$, —CH$_2$C(O)$R^9$, or —CH$_2$C(O)O$R^9$ where $R^9$ is optionally substituted alkyl, cycloalkyl, aryl, heterocycloalkyl or heteroaryl and n is 2-5, X is a palladium reactive functional group or precursor thereof (e.g., X can be acyloxy, hydroxyl, phosphate, phosphate ester, —OS(O)$_2$OH, —OS(O)$_2$O$R^9$ where $R^9$ is optionally substituted alkyl, cycloalkyl, aryl, heterocycloalkyl or heteroaryl, or —O$R^8$ where $R^8$ is a hydroxyl protecting group), $R^2$ is hydrogen or a protecting group, and $R^3$ is hydrogen or a protecting group.

As shown above in Scheme 1, amine 2c can be prepared by reacting 1a with 2b under anhydrous conditions in a suitable solvent, such as benzene, toluene, and the like, in the presence of a drying agent such as activated molecular sieves, magnesium sulfate, sodium sulfate etc. The reaction is preferably conducted at low temperature (i.e. −10 to −5° C.). The resultant imine can be used in the next step without purification or isolation Amine 2c can be synthesized from the imine using a reducing agent, such as sodium borohydride at low temperature (i.e. 0° C.). Cyclization of amine 2c to yield compound 2d can proceed using a catalyst, such as $Pd(PPh_3)_4$. The cyclization reaction can be conducted in a polar solvent, such as acetonitrile, at elevated temperature (i.e. 70° C.). Compound 2d can be purified using standard purification methods (i.e. liquid chromatography). Compound 2e can be synthesized from compound 2d using a palladium-silver catalyzed olefin arylation reaction. Suitable reaction conditions can include $(CH_3CN)_2PdCl_2$ and $AgBF_4$ in the presence of triethylamine in acetonitrile at elevated temperature (e.g. 70° C.). A reducing agent such as sodium borohydride can be used to liberate the catalyst and yield compound 2e. Compound 2e can be purified using standard purification methods (i.e. liquid chromatography). It is contemplated that compound 2e can be further purified using classical resolution (i.e. chromatography, crystallization, fractional crystallization, etc.) known in the art to yield substantially enantiomerically pure compound 2e (i.e. greater than 95%).

Both enantiomers of compounds of formula 2b can be obtained from commercial sources (Aldrich®, USA) or prepared using methods known to one of skill in the art. In some embodiments, compound 2b is of the formula Scheme 1

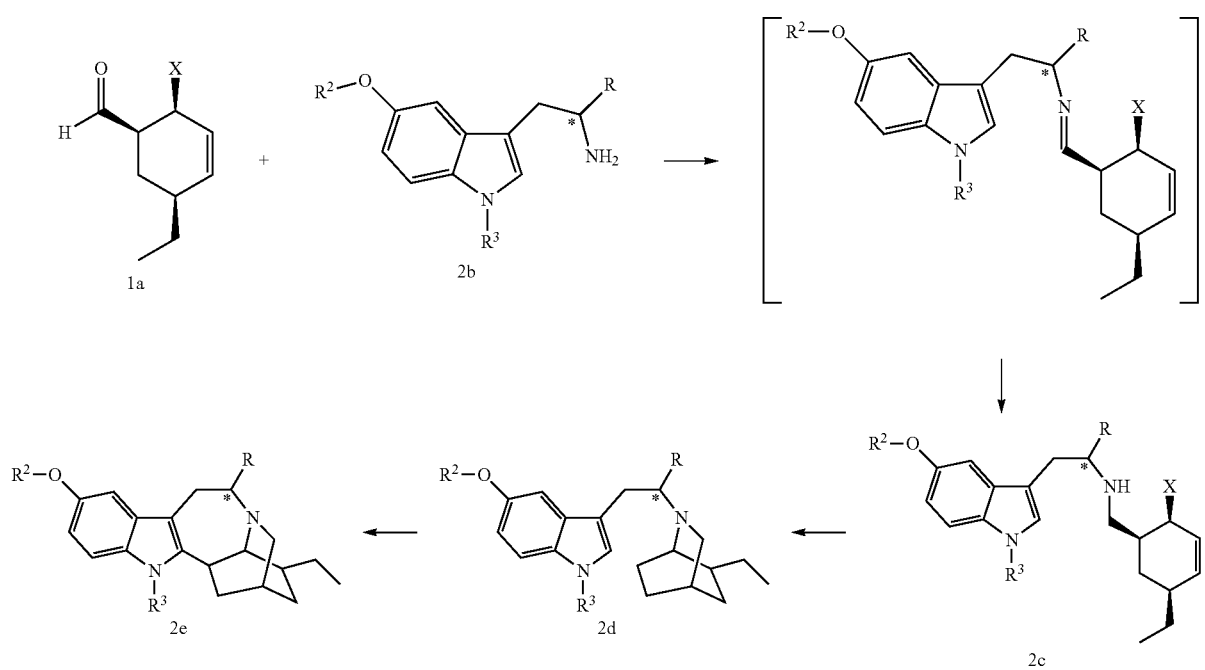

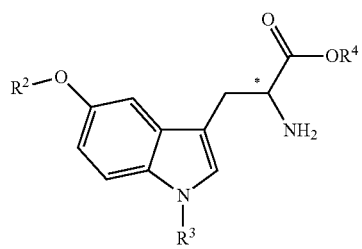

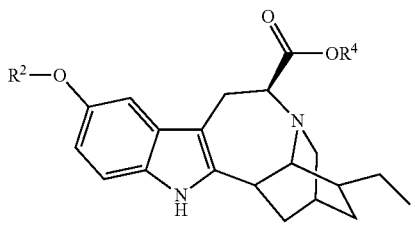

wherein R² and R³ are each independently hydrogen or a protecting group and R⁴ is optionally substituted alkyl or aryl. In certain embodiments, R⁴ is nitrobenzyl or bromobenzyl.

It is contemplated that either the S- or R-configuration of 2b can be used in Scheme 2, above, to afford the diastereomeric compounds R-2e and S-2e, shown below, wherein R² and R⁴ are as described hereinabove.

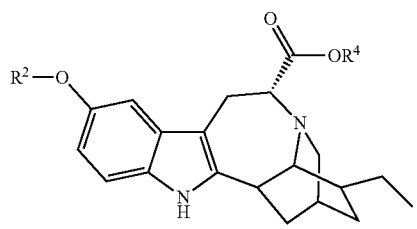

Noribogaine can be prepared from compounds of formula 2e via decarboxylation and deprotection as shown in Scheme 2, below. In Scheme 2, R² is a protecting group and R⁴ is an optionally substituted alkyl, cycloalkyl, aryl, heterocycloalkyl or heteroaryl group, and the indole nitrogen can optionally be protected using an amine protecting group as defined herein. The decarboxylation and deprotection steps can be performed simultaneously or sequentially. In addition, the ester can be hydrolyzed to the carboxylic acid prior to decarboxylation.

Scheme 2

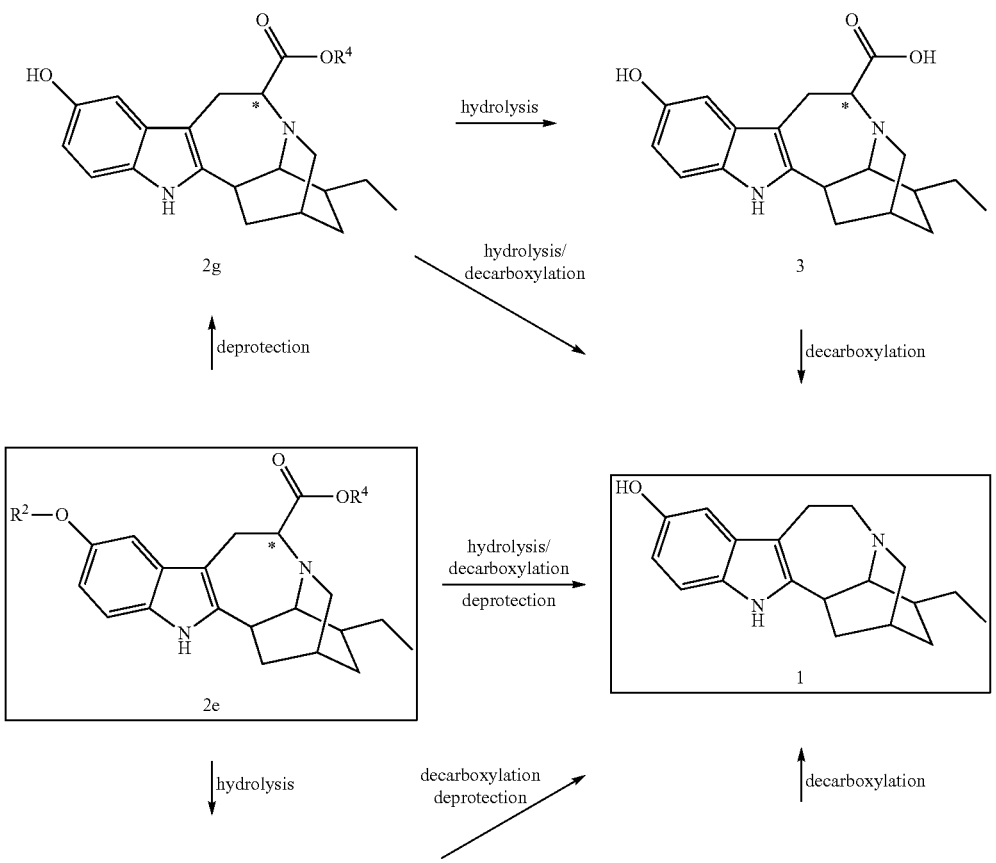

-continued

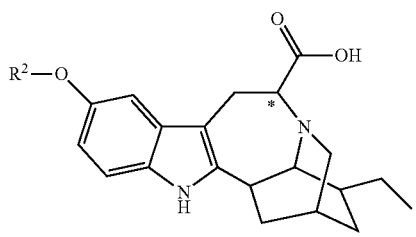

2f

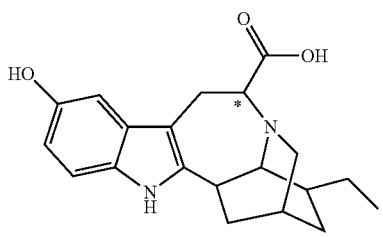

3

The methods disclosed herein provide for the synthesis of stereochemically enriched noribogaine, wherein the enriched stereoisomer is of the 2R, 4S, 5S, 18R configuration. In some embodiments, the 2R, 4S, 5S, 18R noribogaine 1 is provided in at least about 70% the 2R, 4S, 5S, 18R configuration, or at least about 80% the 2R, 4S, 5S, 18R configuration, or at least about 90% the 2R, 4S, 5S, 18R configuration, or at least about 95% the 2R, 4S, 5S, 18R configuration, or at least about 97% the 2R, 4S, 5S, 18R configuration, or at least about 99% the 2R, 4S, 5S, 18R configuration, or at least about 99.5% the 2R, 4S, 5S, 18R configuration.

Accordingly, also provided by the methods disclosed herein, are compounds of formula 3, including compounds of formula R-3 and S-3.

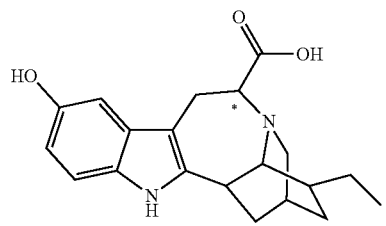

3

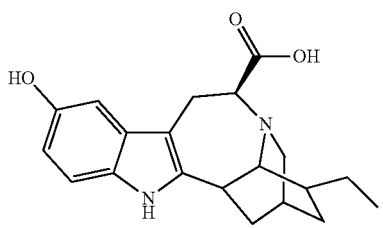

S-3

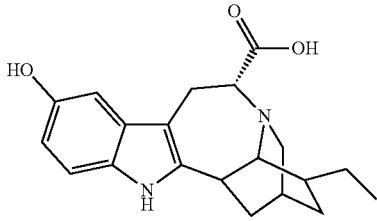

R-3

In some embodiments, the methods disclosed herein further comprise the step of further separating two or more stereoisomers. Such methods for separating stereoisomers (including enantiomers and diastereomers) are known in the art and include chiral column chromatography, chiral resolving agents and the like.

The starting materials for the above reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1 15 (John Wiley and Sons, 1991), Rodd's Chemistry of Carbon Compounds, Volumes 1 5 and Supplementals (Elsevier Science Publishers, 1989), Organic Reactions, Volumes 1 40 (John Wiley and Sons, 1991), March's Advanced Organic Chemistry, (John Wiley and Sons, 4.sup.th Edition), and Larock's Comprehensive Organic Transformations (VCH Publishers Inc., 1989).

It is contemplated that the (1S,4S,6R)-4-ethyl-6-formylcyclohex-2-enyl-1-acetate 1a (where $R^1$ is methyl)

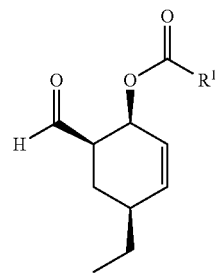

1a for use in the methods disclosed herein can be prepared in about 80% the 1S,4S,6R configuration using literature methods (See Trost et al. *J. Am. Chem. Soc.* 1978, 100:12, 3930-3931). However, it is preferred to have compound 1a in at least 85%, or 90%, or 95%, or greater that 98%, the 1S,4S,6R configuration.

Accordingly, it is contemplated that the compounds of formula 1a to be used in step a) can be prepared via an asymmetric Diels-Alder reaction. The asymmetric Diels-Alder can be performed using a chiral directing group on the diene (i.e., $R^1$ is a chiral directing group as defined herein) (see, Trost, B. M., et al. *J. Org. Chem.* 1978, 43, 4559-4564). Suitable chiral directing groups can be derived from, in particular, chiral alcohols, β-amino alcohols, α- or β-amino acids, and the like. Exemplary groups are shown below, where $R^{20}$ and $R^{21}$ are selected from groups such as optionally substituted alkyl (e.g., methyl, iso-propyl, tert-butyl), aryl (e.g., phenyl, biphenyl, 2,6-dimethylphenyl), heteroaryl (e.g., pyridinyl, oxazolyl, etc.), and $R^{22}$ and $R^{23}$ are selected from hydrogen and groups such as optionally substituted alkyl (e.g., methyl, iso-propyl, tert-butyl), aryl (e.g., phenyl, biphenyl, 2,6-dimethylphenyl), heteroaryl (e.g., pyridinyl, oxazolyl, etc.), or two of $R^{20}$ and $R^{21}$ or $R^{20}$ and $R^{23}$ together with the atom to which they are attached form an optionally substituted cycloalkyl or heterocycloalkyl ring, and further wherein $R^{20}$, $R^{21}$ and $R^{22}$ are different.

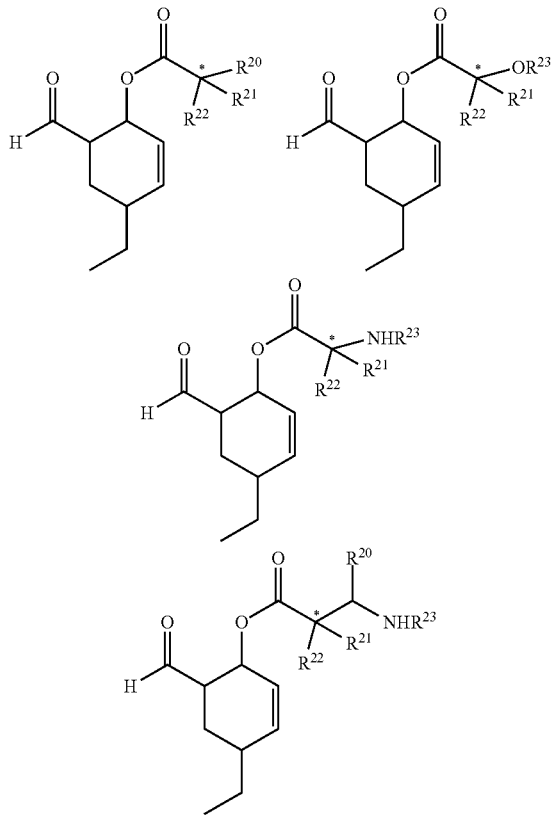

Typically, Diels-Alder reactions utilize a Lewis-acid catalyst. Suitable Lewis-acid catalysts are known in the art, and typically comprise aluminum, titanium, iron, ruthenium, boron, and the like. The Diels-Alder reaction is typically performed under anhydrous conditions which may include a drying agent, such as activated molecular sieves. In some embodiments, the Diels-Alder reaction is performed under pressure in a sealed vessel.

Still further, the asymmetric Diels-Alder reaction can be performed using a chiral Lewis-acid catalyst or a chiral organocatalyst known or prepared by one of skill in the art. Such chiral Lewis-acid catalysts are known in the art, and typically comprise aluminum, titanium, iron, ruthenium, boron, and the like (See, Corey, E. J. Angew. Chem. Int. Ed. 2002, 41, 1650-1667; Yamamoto, H., et al. Angew. Chem. Int. Ed. 2005, 44, 1484-1487; and Kagan, H. B., at al. Chem. Rev. 1992, 92, 1007-1019). Suitable chiral organocatalysts include proline (or derivatives thereof) or α-amino acid derived imidazolidinones.

However, the precise identity of the chiral directing group or the chiral Lewis-acid is not critical to the present invention as such methods for performing asymmetric Diels-Alder reactions have become routine in the art.

The present invention is directed to the compounds and intermediates disclosed herein, including all possible stereoisomers of compounds of formula 1b, 1c, 1d, 1e, 2b, 2c, 2d, 2e, 2f, 2g, and 3. It is contemplated that the compounds of formula 1b, 1c, 1d, 1e, 2b, 2c, 2d, 2e, 2f, 2g, and 3 can be further purified to yield at least 90%, or at least 95%, or at least 98%, of single stereoisomer using chiral resolution methods, such as chiral chromatography and/or crystallization of the diastereomeric salt using a chiral acid, such as tartaric acid, mandelic acid, lactic acid, and the like. Such methods are routine in the art.

The synthetic noribogaine of the present invention is distinguished from plant derived noribogaine (i.e. noribogaine synthesized from naturally occurring ibogaine) by its $^{14}C$ content. $^{14}C$ has a half-life of about 5,730 years and is generated in the upper atmosphere as $^{14}CO_2$. The amount of $^{14}CO_2$ present is approximately 1 ppt (parts per trillion) and, through photosynthesis, accumulates in plants resulting in a $^{14}C$ content of plant material of approximately 1 ppt. Accordingly, plant derived noribogaine (i.e. noribogaine synthesized from naturally occurring ibogaine) is expected to have approximately 1 ppt $^{14}C$. Conversely, the noribogaine and intermediates disclosed herein are derived from fossil fuels, which due to $^{14}C$ decay, would have a $^{14}C$ content of less than 1 ppt, or less than 0.9 ppt $^{14}C$. Accordingly, provided herein is noribogaine having a $^{14}C$ content of less than 1 ppt, or less than 0.9 ppt, or less than 0.8 ppt, or less than 0.7 ppt, or less than 0.6 ppt, or less than 0.5 ppt, or less than 0.4 ppt, or less than 0.3 ppt, or less than 0.2 ppt, or less than 0.1 ppt. The amount of $^{14}C$ can be analyzed using methods well known in the art (i.e. radiocarbon analyses can be carried out according to the American Society for Testing Materials ASTM D6866 procedure (ASTM international, 100 Barr Harbon Drive, PO Box C700, West Conshohocken, Pa. 19428-2959)). Furthermore, provided is a method for distinguishing synthetic noribogaine from plant derived noribogaine based on the $^{14}C$ content.

It will be apparent to those skilled in the art that many modifications of the above exemplifying methods, both to materials and methods, may be practiced without departing from the scope of the current invention.

Treatment of Pain

In one of its method aspect, the present invention is directed to a method for treating a pain in a patient which method comprises administering to said patient a compound of this invention or a pharmaceutically acceptable salt thereof or a pharmaceutical composition comprising a compound of this invention and a pharmaceutically acceptable excipient. The pain can be any type of pain including, but not limited to neuropathic or nociceptive pain, and various types thereof including somatic, visceral and phantom pain.

Treatment of Addiction

In another of its method aspect, the present invention is directed to a method for treating addiction in a patient which method comprises administering to said patient a compound of this invention or a pharmaceutically acceptable salt thereof or a composition comprising a compound of this invention and a pharmaceutically acceptable excipient.

In certain embodiments, the treatment of addiction in a patient comprises alleviating the symptoms associated with withdrawal from drug dependency. Such symptoms include nausea, vomiting, anxiety, abdominal cramps, muscle pain, chills and headache. In addition, it is contemplated that treatment with a compound of this invention decreases the drug cravings normally experienced by addicts after cessation of the self administration of the abused substance. It is contemplated that the compositions disclosed herein are especially useful in the treatment of addiction to narcotics such as heroin and methadone. However, it is also useful in treating patients addicted to cocaine, alcohol, amphetamines and combinations of these drugs.

The invention is also directed to a method for treating drug addiction (involving drug dependency or drug abuse) during withdrawal therapy by administering a compound of this invention to a patient at a dosage sufficient to reduce or eliminate one or more symptoms associated with withdrawal. Such symptoms include nausea, vomiting, anxiety, abdominal cramps, muscle pain, chills and headache. In addition, treatment with a compound of this invention is contemplated to decrease the drug cravings normally experienced by addicts after cessation of the self administration of the abused substance, for example, narcotics such as heroin and methadone. However, compounds of this invention are contemplated to be also useful in treating patients addicted to cocaine, alcohol, amphetamines and combinations of these drugs. Compounds of this invention may be administered to patients suffering from drug dependence or abuse in conjunction with an opioid antagonist such as naloxone, naltrexone or nalorphine, for example, at a concentration of between 0.15 mg and 0.5 mg for each mg of the compound of this invention administered.

pconventional drug withdrawal therapy, specifically providing for the administration of a compound of this invention with one or more opioid antagonists.

What is claimed is:

1. A method for preparing a compound of formula 1:

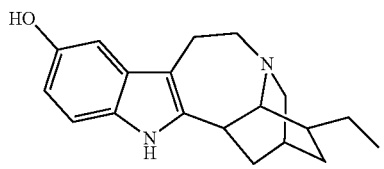

1 or a salt thereof, which method comprises the steps of:
a) contacting a compound of formula 1a with a compound of formula 1b, wherein X is a palladium reactive functional group or precursor thereof, $R^2$ and $R^3$ are each independently hydrogen or a protecting group and wherein 1a is at least 95% the 1S,4S,6R configuration,

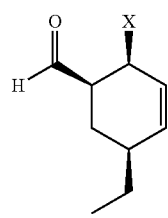

1a

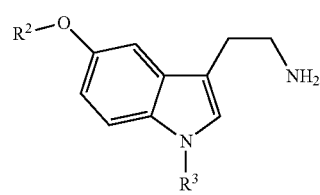

1b under anhydrous reductive amination reaction conditions to yield a compound of formula 1c:

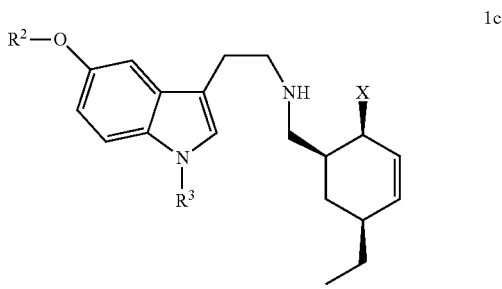

1c b) contacting a compound of formula 1c with a cyclization catalyst under cyclizing conditions to yield a compound of formula 1d:

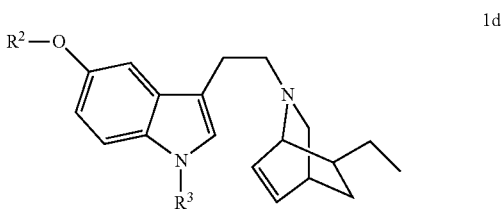

1d c) contacting a compound of formula 1d under olefin arylation conditions to yield a compound of formula 1e:

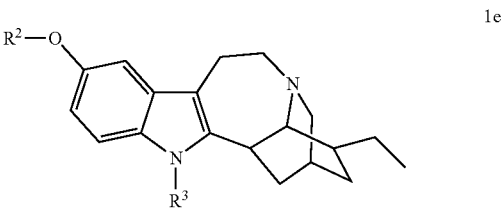

1e d) contacting a compound of formula 1e under deprotection conditions to yield a compound of formula 1; and
e) optionally converting compound of formula 1 to a salt thereof.

2. A method for preparing a compound of formula 2e

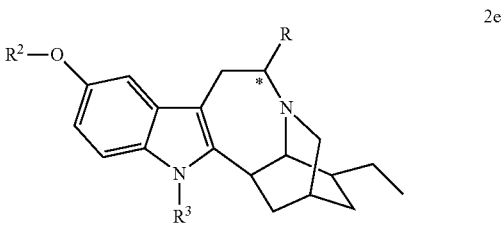

2e or a salt thereof, which method comprises:
a) contacting a compound of formula 1a with a compound of formula 2b, wherein
R is selected from the group consisting of carboxyl, carboxyl ester, amide, phosphonate, phosphonate ester, a peptide, a peptidomimetic, a biodegradable, biocompatible polymer, and —C(O)R⁸ where R⁸ is —NH(CH₂)ₙS(O)₂OH, —NH(CH₂)ₙOH, —C(O)R⁹, —OC(O)R⁹, —CH₂C(O)R⁹, or —CH₂C(O)OR⁹ where R⁹ is optionally substituted alkyl, cycloalkyl, aryl, heterocycloalkyl or heteroaryl and n is 2-5, X is a palladium reactive functional group or precursor thereof, R² is hydrogen or a protecting group, and R³ is hydrogen or a protecting group, and further wherein the * denotes a stereogenic carbon having greater than 95% of one enantiomer,

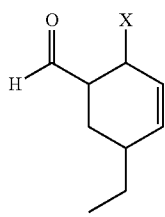

1a

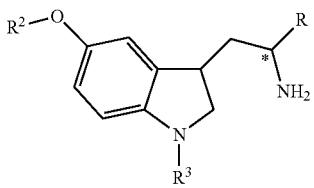

2b under reductive amination conditions to yield a compound of formula 2c:

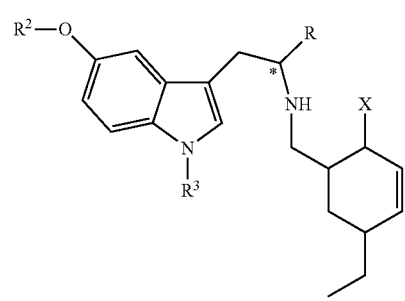

2c b) contacting a compound of formula 2c with a cyclization catalyst under cyclization conditions to yield a compound of formula 2d:

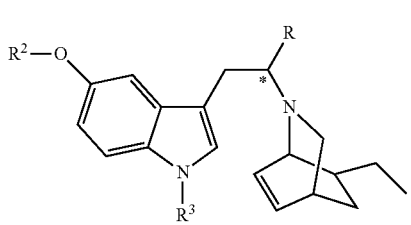

2d c) contacting a compound of formula 2d under olefin arylation conditions to yield a compound of formula 2e:

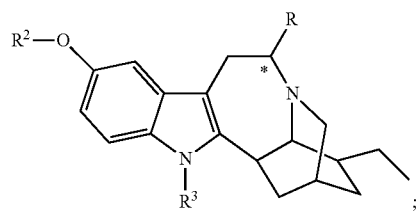

2e and d) optionally converting compound of formula 2e to a salt thereof.

3. A method for preparing a compound of formula 1:

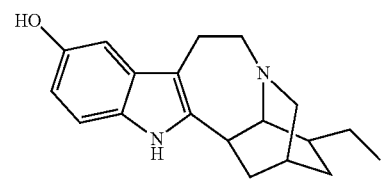

1 which method comprises:
a) contacting a compound of formula 2e, wherein
R is selected from the group consisting of carboxyl and carboxyl ester,
R² is hydrogen or a protecting group, and
R³ is hydrogen or a protecting group, and
further wherein the * denotes a stereogenic carbon having greater than 95% of one enantiomer,

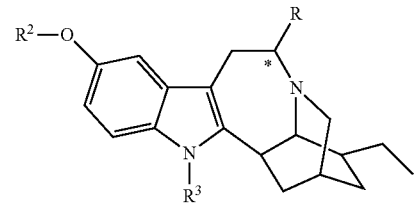

2e under decarboxylation conditions to yield a compound of formula 1e:

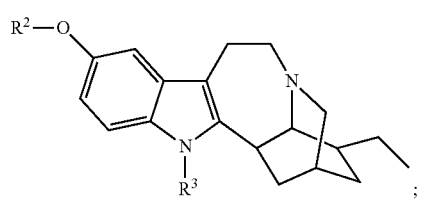

1e and
b) optionally contacting a compound of formula 1e under deprotection conditions to yield a compound of formula 1.

4. The method of claim 1, wherein greater than 90% of the compound of Formula 1 is of the 2R, 4S, 5S, 18R stereochemical configuration.

5. The method of claim 1, wherein greater than 95% of the compound of Formula 1 is of the 2R, 4S, 5S, 18R stereochemical configuration.

6. The method of claim 1, wherein greater than 99% of the compound of Formula 1 is of the 2R, 4S, 5S, 18R stereochemical configuration.

7. The method of claim 1, wherein the method further comprises the step of separating two or more stereoisomers.

8. The method of claim 2, wherein compound 2b is of the formula:

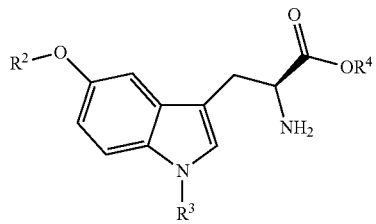

wherein $R^2$ and $R^3$ are each independently hydrogen or a protecting group and $R^4$ is optionally substituted alkyl or aryl.

9. The method of claim 2, wherein compound 2b is of the formula:

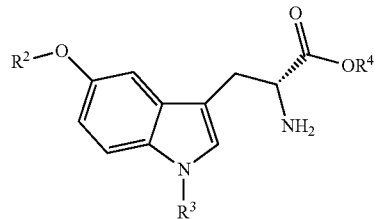

wherein $R^2$ and $R^3$ are each independently hydrogen or a protecting group and $R^4$ is optionally substituted alkyl or aryl.

* * * * *